United States Patent [19]
Gerdes et al.

[11] Patent Number: 5,977,123
[45] Date of Patent: Nov. 2, 1999

[54] OXIMETHER AND ACRYLIC ACID DERIVATIVES AND THEIR USE AS FUNGICIDES

[75] Inventors: Peter Gerdes, Aachen; Herbert Gayer, Monheim; Ulrich Heinemann, Leichlingen; Ralf Tiemann, Leverkusen; Klaus Stenzel, Düsseldorf; Stefan Dutzmann, Langenfeld, all of Germany

[73] Assignee: Bayer Aktiengesellscgaft, Leverkusen, Germany

[21] Appl. No.: 08/981,971

[22] PCT Filed: Jul. 4, 1996

[86] PCT No.: PCT/EP96/02931

§ 371 Date: Jan. 9, 1998

§ 102(e) Date: Jan. 9, 1999

[87] PCT Pub. No.: WO97/03950

PCT Pub. Date: Feb. 6, 1997

[30] Foreign Application Priority Data

Jul. 17, 1995 [DE] Germany .............. 195 25 969

[51] Int. Cl.$^6$ ............... C07C 255/62; C07D 239/34; C07D 285/18; A01N 37/34
[52] U.S. Cl. ............. 514/269; 514/342; 514/351; 514/439; 514/514; 514/521; 514/533; 514/539; 544/319; 546/268.7; 546/300; 548/129; 558/14; 558/405; 558/406; 560/15; 560/35

[58] Field of Search ............. 514/514, 521, 514/533, 539, 269, 342, 351, 439; 558/14, 405, 406; 560/15, 35; 544/319; 546/268.7, 300; 548/129

[56] References Cited

FOREIGN PATENT DOCUMENTS

| 461797 | 12/1991 | European Pat. Off. . |
| 44247788 | 6/1995 | Germany .............. 560/35 |
| 4424788 | 6/1995 | Germany . |

*Primary Examiner*—Mukund J. Shah
*Assistant Examiner*—Deepak R. Rao
*Attorney, Agent, or Firm*—Sprung Kramer Schaefer & Briscoe

[57] ABSTRACT

The invention relates to novel oximether and acrylic acid derivatives of the formula (I)

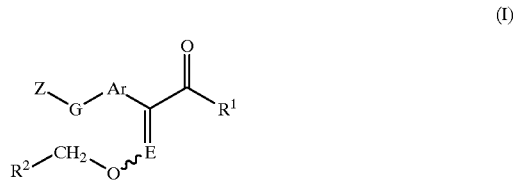

in which Z, G, Ar, E, $R^1$ and $R^2$ have the meanings as given in the specification, to processes for their preparation and to their use as fungicides.

10 Claims, No Drawings

OXIMETHER AND ACRYLIC ACID DERIVATIVES AND THEIR USE AS FUNGICIDES

This application is a 371 of PCT/EP96/02931 filed Jul. 4. 1996.

The invention relates to novel ether derivatives, to a plurality of processes for their preparation and to their use as fungicides, and to novel intermediates and to a plurality of processes for their preparation.

Certain methoximinoacetic acid and methoxyacrylic acid derivatives of a constitution similar to the ether derivatives described hereinbelow are known to have fungicidal properties (cf. for example EP-A-226 917 or EP-A-370 629 or EP-A-398 692). However, in many instances the fungicidal activity of these compounds is unsatisfactory.

This invention, accordingly, provides the novel ether derivatives of the general formula (I)

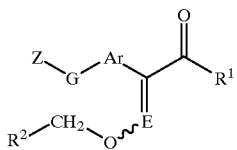

(I)

in which
Ar represents respectively optionally substituted arylene or heteroarylene,
E represents =CH— or nitrogen,
G represents a single bond, represents oxygen, sulphur or represents respectively optionally halogen-, hydroxyl-, alkyl-, halogenoalkyl- or cycloalkyl-substituted alkanediyl, alkenediyl, alkinediyl or one of the groupings below —Q—CQ—, —CQ—Q—, —CH$_2$—Q—; —Q—CH$_2$—, —CQ—Q—CH$_2$—, —CH$_2$—Q— CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N— O—CH$_2$—, —N(R$^4$)—, —CQ—N(R$^4$)—, —N(R$^4$)— CQ—, —Q—CQ—N(R$^4$)—, —N=C(R$^3$)—Q— CH$_2$—, —CH$_2$—O—N=C(R$^3$)—, —C(CH$_3$)—O— NOC(R$^3$), —N(R$^4$)—CQ—Q—, —CQ—N(R$^4$)— CQ—Q—, —N(R$^4$)—CQ—Q—CH$_2$—, —Q—C(R$^3$) =N—O—CH$_2$—, —N(R$^4$)—C(R$^3$)=N—O—CH$_2$—, —O—CH$_2$—C(R$^3$)=N—O—CH$_2$—, —N=N—C (R$^3$)=N—O—CH$_2$—, —C(=N—O—R$^5$)—C(R$^3$) =N—O—CH$_2$—, —C(=N—O—R$^5$)—C(R$^3$)—O— N=CH—, —C(=N—O—R$^5$)—C(R$^3$)—O—N=C (CH$_3$)—, —T—Ar$^1$— or —T—Ar$^1$—Q—, where
Ar$^1$ represents optionally substituted arylene, heteroarylene, cycloalkylene or heterocycloalkylene (i.e. an aliphatic ring which is doubly attached and in which one or more carbon atoms are replaced by hetero atoms, i.e. atoms that differ from carbon),
n represents the numbers 0, 1 or 2,
Q represents oxygen or sulphur,
R$^3$ represents hydrogen, cyano or respectively optionally substituted alkyl, alkoxy, alkylthio, alkylamino, dialkylamino or cycloalkyl, and
R$^4$ represents hydrogen, hydroxyl, cyano or respectively optionally substituted alkyl, alkoxy or cycloalkyl, and
R$^5$ represents hydrogen or alkyl, and
T represents a single bond, represents oxygen, sulphur, —CH$_2$—O—, —CH$_2$—S— or represents optionally substituted alkanediyl, R$^1$ represents alkoxy, alkylamino or dialkylamino,
R$^2$ represents cyano, thiocyanato, alkylcarbonyl, alkoxycarbonyl, aminocarbonyl, aminothicarbonyl, alkylamiinocarbonyl or dialkylaminocarbonyl, and
Z represents respectively optionally substituted alkyl, alkenyl, alkinyl, cycloalkyl, aryl or heterocyclyl.

In the definitions, the saturated or unsaturated hydrocarbon chains, such as alkyl, alkenyl or alkinyl, are in each case straight-chain or branched, including in combination with hetero atoms, such as in alkoxy, alkylthio or alkylamino.

Halogen generally represents fluorine, chlorine, bromine or iodine, preferably fluorine, chlorine or bromine, in particular fluorine or chlorine.

Aryl represents aromatic, mono- or polycyclic hydrocarbon rings, for example preferably phenyl, naphthyl, anthranyl, phenanthryl, preferably phenyl or naphthyl, in particular phenyl.

Heterocyclyl represents saturated or unsaturated, and aromatic, ring-shaped compounds in which at least one ring member is a hetero atom, i.e. an atom different from carbon. If the ring contains more than one hetero atom, these may be identical or different. Preferred hetero atoms are oxygen, nitrogen or sulphur. Optionally, the ring-shaped compounds form a polycyclic ring system together with other carbocyclic or heterocyclic fused or bridged rings. Preference is given to mono- or bicyclic ring systems, in particular to mono- or bicyclic aromatic ring systems.

Cycloalkyl represents saturated carbocyclic ring-shaped compounds which optionally, together with other carbocyclic, fused or bridged rings, form a polycyclic ring system.

Furthermore, it has been found that the novel ether derivatives of the general formula (I) are obtained when
a) hydroxyl compounds of the general formula (II)

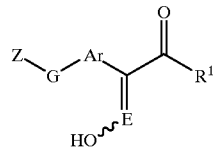

(II)

in which
Ar, E, G, R$^1$ and Z are each as defined above are reacted with a halogen compound of the general formula (III)

X$^1$—CH$_2$—R$^2$ (III)

in which
X$^1$ represents halogen and
R$^2$ is as defined above,
if appropriate in the presence of an acid acceptor and if appropriate in the presence of a diluent; or when
b) hydroxyaryl compounds of the general formula (IV)

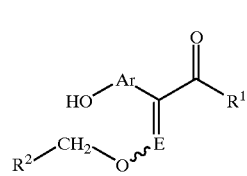

(IV)

in which
Ar, E, R$^1$ and R$^2$ are each as defined above, are reacted with an aryl compound of the general formula (V)

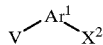 (V)

in which
Ar¹ is as defined above,
V represents halogen or Z—T—, where
Z and T are each as defined above, and
X² represents halogen, alkylsulphonyl or arylsulphonyl,
if appropriate in the presence of an acid acceptor and if appropriate in the presence of a diluent.

Finally, it has been found that the novel ether derivatives of the general formula (I) have very strong fungicidal activity.

The compounds according to the invention may be present as mixtures of various possible isomeric forms, in particular of stereoisomers, such as, for example, E- and Z-. Both the E- and the Z-isomers, and any mixtures of these isomers, are claimed.

The formula (I) provides a general definition of the ether derivatives according to the invention. The individual definitions in this formula are defined by way of preference and in each case independently of the others, and:

Ar preferably represents respectively optionally substituted phenylene or naphthylene, represents mono- or bicyclic heteroarylene having in each case 5 or 6 ring members or represents benzo-fused heteroarylene having 5 or 6 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxy, carbamoyl, thiocarbamoyl, respectively straight-chain or branched alkyl, alkoxy, alkylthio, alkylsulphinyl or alkylsulphonyl having in each case 1 to 6 carbon atoms, respectively straight-chain or branched alkenyl, alkenyloxy or alkinyloxy having in each case 2 to 6 carbon atoms, respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, respectively straight-chain or branched halogenoalkenyl or halogenoalkenyloxy having in each case 2 to 6 carbon atoms and 1 to 11 identical or different halogen atoms, respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is doubly attached and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms.

E preferably represents =CH— or nitrogen.

G preferably represents a single bond, represents oxygen, sulphur or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or one of the groupings below —Q—CQ—, —CQ—Q—, —CH₂—; —Q—CH₂—, —CQ—CH₂—, —CH₂—Q—CQ—, —Q—CQ—CH₂—, —Q—CQ—Q—CH₂—, —N=N—, —S(O)$_n$—, —CH₂—S(O)$_n$—, —CQ—, —S(O)$_n$—CH₂—, —C($R^3$)=N—O—, —C($R^3$)=N—O—CH₂—, —N($R^4$)—, —CQ—N($R^4$)—, —N($R^4$)—CQ—, —Q—CQ—N($R^4$)—, —N=C($R^3$)—Q—CH₂—, —CH₂—O—N=C($R^3$)—, —C(CH₃)—O—N=C($R^3$)—, —N($R^4$)—CQ—Q—, —CQ—N($R^4$)—CQ—Q—, —N($R^4$) —CQ—Q—CH₂—, —Q—C($R^3$)=N—O—CH₂—, —N($R^4$)—C($R^3$)=N—O—CH₂—, —O—CH₂—C($R^3$)=N—OCH₂—, —N=N—C($R^3$)=N—O—CH₂—, —C(=N—O—$R^5$)—C($R^3$)=N—OCH₂—, —C(=N—O—$R^5$)—C($R^3$)—O—N=CH—, —C(=N—O—$R^5$)—C($R^3$)—O—N=C(CH₃)—, —T—Ar¹ or —T—Ar¹—Q—, where n represents the numbers 0, 1 or 2, Q represents oxygen or sulphur, $R^3$ represents hydrogen, cyano, represents respectively optionally halogen-, cyano- or $C_1$–$C_1$-alkoxy-substituted alkyl, alkoxy, alkylthio, alkylamino or dialkylamino having in each case 1 to 6 carbon atoms in the alkyl groups or represents respectively optionally halogen-, cyano-, carboxy-, $C_1$–$C_1$-alkyl- or $C_1$–$C_1$-alkoxy-carbonyl-substituted cycloalkyl having 3 to 6 carbon atoms, and $R^4$ represents hydrogen, hydroxyl, cyano or represents optionally halogen-, cyano- or $C_1$–$C_1$-alkoxy-substituted alkyl having 1 to 6 carbon atoms or represents optionally halogen-, cyano-, carboxy-, $C_1$–$C_4$-alkyl- or $C_1$–$C_4$-alkoxy-carbonyl-substituted cycloalkyl having 3 to 6 carbon atoms, $R^5$ represents hydrogen or alkyl having 1 to 4 carbon atoms, Ar¹ represents phenylene, naphthylene, cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, the possible substituents preferably being selected from the list below:

halogen, cyano, nitro, amino, hydroxyl, formyl, carboxy, carbamoyl, thiocarbamoyl;
respectively straight-chain or branched alkyl, alkoxy, alkylthio, alkylsulphinyl or alkylsulphonyl having in each case 1 to 6 carbon atoms;
respectively straight-chain or branched alkenyl or alkenyloxy having in each case 2 to 6 carbon atoms;
respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;
respectively straight-chain or branched halogenoalkenyl or halogenoalkenyloxy having in each case 2 to 6 carbon atoms and 1 to 11 identical or different halogen atoms;
respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and;
cycloalkyl having 3 to 6 carbon atoms and T represents a single bond, represents oxygen, sulphur, —CH₂—O—, —CH₂—S— or represents alkanediyl having 1 to 3 carbon atoms, $R^1$ preferably represents alkyl, alkoxy, alkylamino or dialkylamino having 1 to 4 carbon atoms in the respective alkyl chains.

$R^2$ preferably represents cyano, thiocyanato, aminocarbonyl, aminothiocarbonyl, or represents alkylcarbonyl, alkoxycarbonyl, alkylaminocarbonyl or dialkylaminocarbonyl having 1 to 4 carbon atoms in the respective alkyl chains, Z preferably represents alkyl having 1 to 8 carbon atoms which is optionally mono- or polysubstituted by identical or different substituents selected from the group consisting of halogen, cyano, hydroxyl, amino, $C_1$–$C_4$-alkoxy, $C_1$–$C_4$-alkylthio, $C_1$–$C_4$-alkylsulphinyl and $C_1$–$C_4$-alkylsulphonyl (each of which is optionally substituted by halogen);

represents respectively optionally halogen-substituted alkenyl or alkinyl having in each case up to 8 carbon atoms;

represents cycloalkyl having 3 to 6 carbon atoms each of which is optionally mono- or polysubstituted by identical or different substituents selected from the group consisting of halogen, cyano, carboxy, phenyl (which is optionally substituted by halogen, cyano, $C_1$–$C_4$-alkyl, $C_1$–$C_4$-halogenoalkyl, $C_1$–$C_4$-alkoxy or $C_1$–$C_4$-halogenoalkoxy), $C_1$–$C_4$-alkyl and $C_1$–$C_4$-alkoxy-carbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, the possible substituents preferably being selected from the list below: halogen, cyano, nitro, amino, hydroxyl, formyl, carboxy, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 11 identical or different halogen atoms;

respectively straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

alkylene or dioxyalkylene, each of which has 1 to 6 carbon atoms, is doubly attached and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

heterocyclyl or heterocyclyl-methyl having in each case 3 to 7 ring members, 1 to 3 of which are in each case identical or different hetero atoms—in particular nitrogen, oxygen and/or sulphur—or a grouping

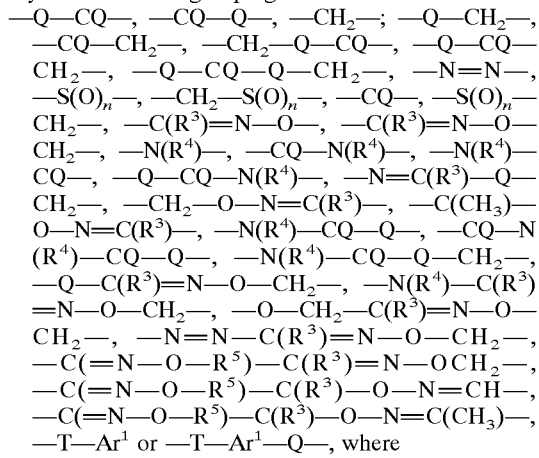

in which $A^1$ represents alkyl having 1 to 4 carbon atoms or cycloalkyl having 1 to 6 carbon atoms and $A^2$ represents optionally cyano-, alkoxy-, alkylthio-, alkylamino-, dialkylamino- or phenyl-substituted alkyl having 1 to 4 carbon atoms, alkenyl or alkinyl having in each case 2 to 4 carbon atoms.

Ar in particular represents ortho-, meta- or para-phenylene, furandiyl, thiophenediyl, pyrrolediyl, pyrazolediyl, triazolediyl, oxazolediyl, isoxazolediyl, thiazolediyl, isothiazolediyl, oxadiazolediyl, thiadiazolediyl, pyridinediyl (in particular pyridine-2, 3-diyl), pyrimidinediyl, pyridazinediyl, pyrazinediyl, 1,3,4-triazinediyl or 1,2,3-triazinediyl, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl.

E in particular represents =CH— or nitrogen.

G in particular represents oxygen or represents respectively optionally fluorine-, chlorine- or bromine-substituted dimethylene (ethane-1,2-diyl), ethene-1,2-diyl or one of the groupings below —Q—CQ—, —CQ—Q—, —CH$_2$—; —Q—CH$_2$—, —CQ—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—OCH$_2$—, —C(=N—O—R$^5$)—C(R$^3$)—O—N=CH—, —C(=N—O—R$^5$)—C(R$^3$)—O—N=C(CH$_3$)—, —T—Ar$^1$ or —T—Ar$^1$—Q—, where n represents the numbers 0, 1 or 2, Q represents oxygen or sulphur, $R^3$ represents hydrogen, cyano, methyl, ethyl or cyclopropyl and $R^4$ represents hydrogen, methyl, ethyl or cyclopropyl, $R^5$ represents hydrogen or methyl, Ar$^1$ represents phenylene or pyridinediyl, each of which is optionally mono- to trisubstituted by identical or different substituents, represents respectively optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, the possible substituents preferably being selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl and T represents a single bond, represents oxygen, sulphur, —CH$_2$—O—, CH$_2$—S—, methylene, ethylene or propylene.

R$^1$ in particular represents methyl, ethyl, n- or i-propyl, methoxy, ethoxy, n- or i-propoxy-, methylamino, ethylamino, n- or i-propylamino, dimethylamino, diethylamino or N-methyl-N-ethylamino.

R$^2$ in particular represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl.

Z in particular represents phenyl, 1,2,4-thiadiazolyl, 1,3,4-thiadiazolyl, 1,2,4-oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methylenedioxy, ethylenedioxy, each of which is doubly attached and each of which is optionally mono- to tetrasubstituted by identical or different substituents selected from the group consisting of fluorine, chlorine, methyl, trifluoromethyl and ethyl or a grouping

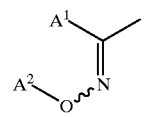

A$^1$ in particular represents methyl, ethyl, n- or i-propyl, n-, i-, s- or t-butyl, cyclopropyl or cyclobutyl, A$^2$ in particular represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

A particularly preferred group of compounds according to the invention are those compounds of the formula (I) in which Ar represents ortho-phenylene, pyridine-2,3-diyl or thiophene-2,3-diyl, E represents =CH— or nitrogen, G represents —O—CH$_2$—, R$^1$ represents methoxy or methylamino, R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, and Z represents phenyl which is in each case optionally mono- to trisubstituted by identical or different substituents, the possible substituents preferably being selected from the list below: fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methylenedioxy or ethylenedioxy, each of which is doubly attached and each of which is optionally mono- to tetrasubstituted by identical or different substituents selected from the group consisting of fluorine, chlorine, methyl, trifluoromethyl or ethyl or a grouping

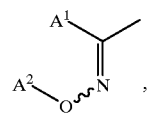

in which

A$^1$ represents methyl, ethyl, n- or i-propyl, n-, i-, s- or t-butyl, cyclopropyl or cyclobutyl and A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylamninomethyl, dimethylaminoethyl, methylaminomethyl, methylaminoethyl or benzyl.

A group of compounds according to the invention which is likewise particularly preferred are those compounds of the formula (I)

in which

Ar represents ortho-phenylene, pyridine-2,3-diyl or thiophene-2,3-diyl,

E represents =CH— or nitrogen,

G represents —C(R$^3$)=N—O—CH$_2$—,

R$^3$ represents methyl or cyclopropyl,

R$^1$ represents methoxy or methylamino,

R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, and Z represents phenyl, pyridyl or pyrimidyl, each of which is optionally mono- to trisubstituted by identical or different substituents, the possible substituents preferably being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is doubly attached and each of which is optionally mono- to tetrasubstituted by identical or different substituents selected from the group consisting of fluorine, chlorine, methyl, trifluoromethyl and ethyl.

A group of compounds according to the invention which is furthermore particularly preferred are those compounds of the formula (I)

in which

Ar represents ortho-phenylene,

E represents =CH— or nitrogen,

G represents oxygen or —T—Ar$^1$—O—,

Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, trifluoromethoxy, difluorochloromethoxy, R$^1$ represents methoxy or methylamino, R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, T represents a single bond, represents oxygen, sulphur, —CH$_2$—O—, CH$_2$—S—, methylene, ethylene or propylene, and Z represents phenyl, pyridyl, pyrimidyl or thienyl, each of which is optionally mono- to trisubstituted by identical or different substituents selected from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy and methylenedioxy or ethylenedioxy, each of which is doubly attached and each of which is optionally mono- to tetrasubstituted by identical or different substituents selected from the group consisting of fluorine, chlorine, methyl, trifluoromethyl and ethyl.

The abovementioned general or preferred radical definitions apply both to the end products of the formula (I) and, correspondingly, to the starting materials or intermediates required in each case for the preparation.

These radical definitions can be combined with each other as desired, that is to say combinations between the stated ranges of preferred compounds are also possible.

Examples of the compounds according to the invention are listed in Tables 1 to 16:

TABLE 1
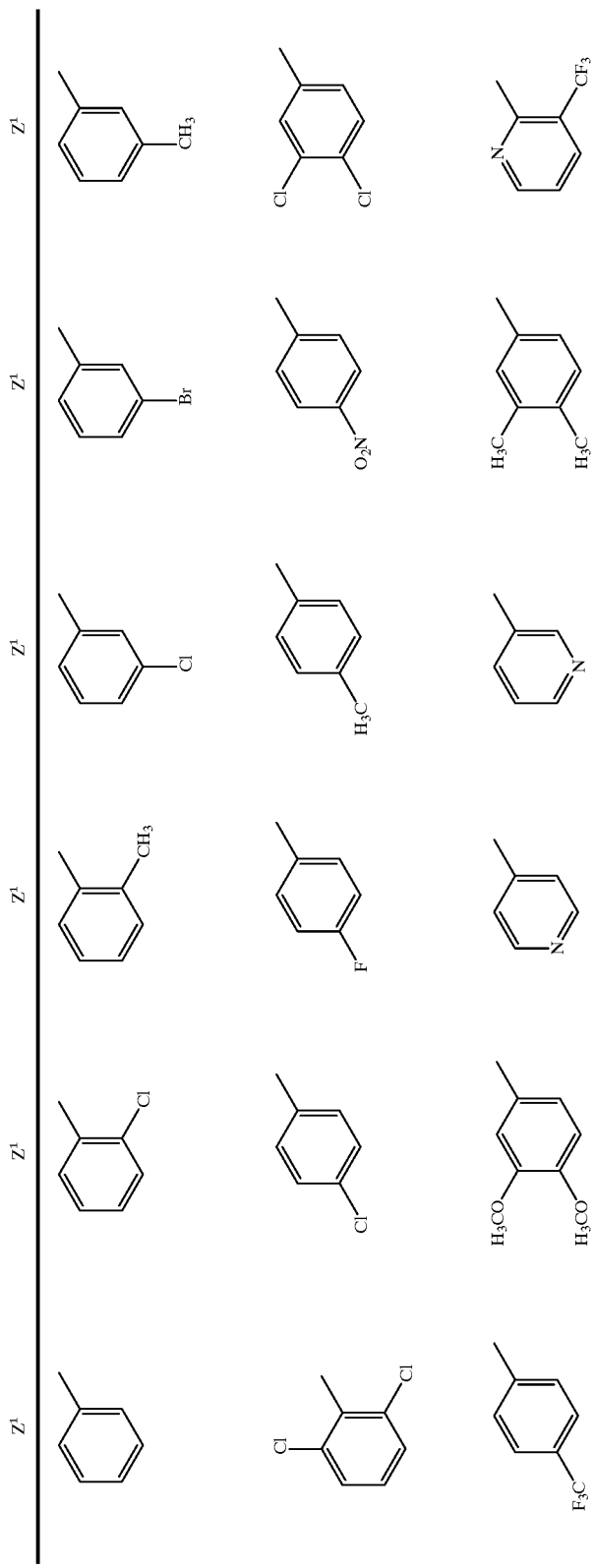

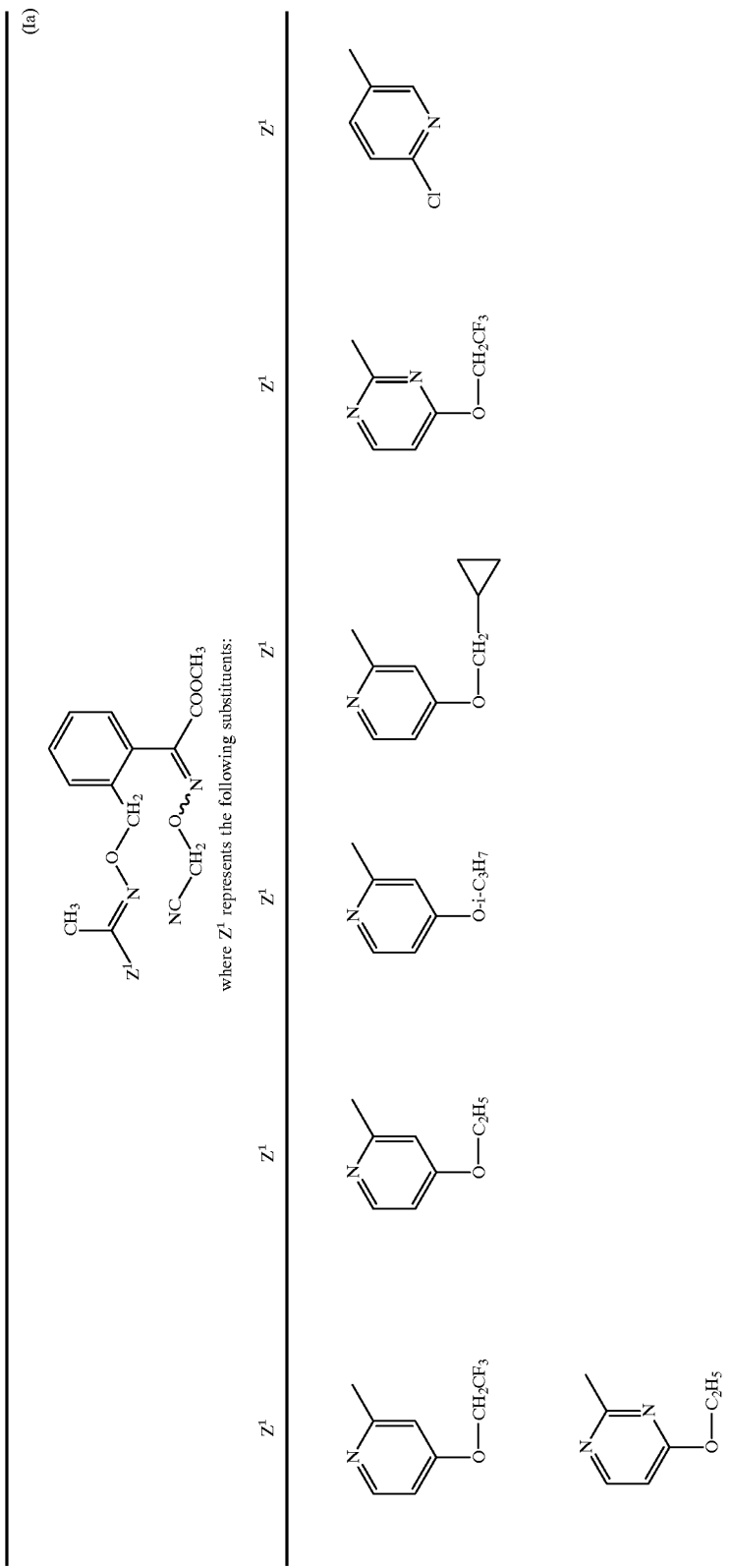

TABLE 2

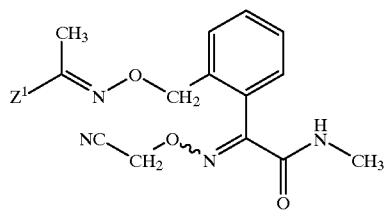
(I-b)

where $Z^1$ represents the substituents mentioned in Table 1.

TABLE 3

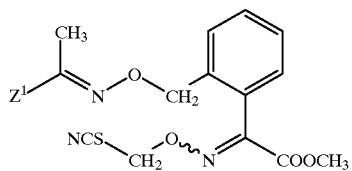
(I-c)

where $Z^1$ represents the substituents mentioned in Table 1.

TABLE 4

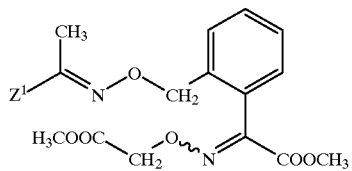
(I-d)

where $Z^1$ represents the substituents mentioned in Table 1.

TABLE 5

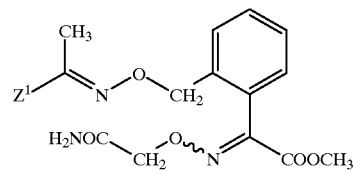
(I-e)

where $Z^1$ represents the substituents mentioned in Table 1.

TABLE 6

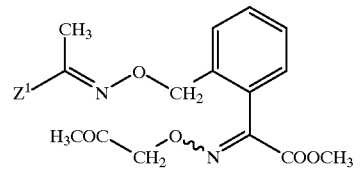
(I-f)

where $Z^1$ represents the substituents mentioned in Table 1.

TABLE 7

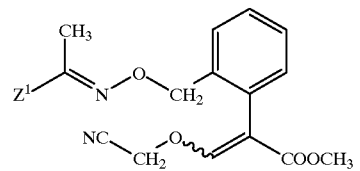
(I-g)

where $Z^1$ represents the substituents mentioned in Table 1.

TABLE 8
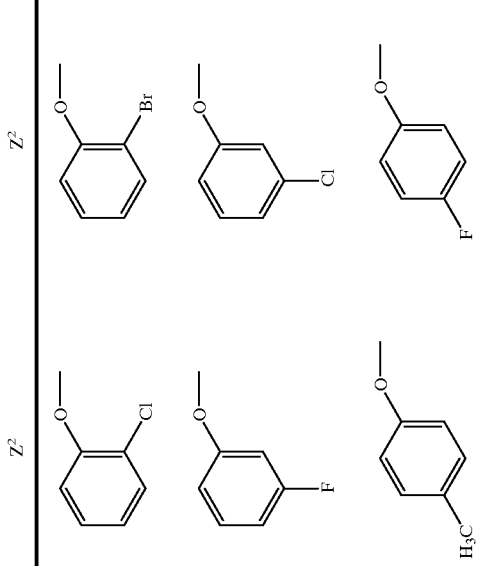
(I-h)
where $Z^2$ represents the following substituents:
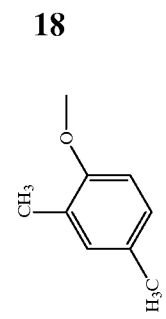
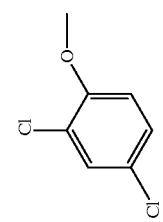
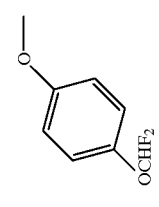
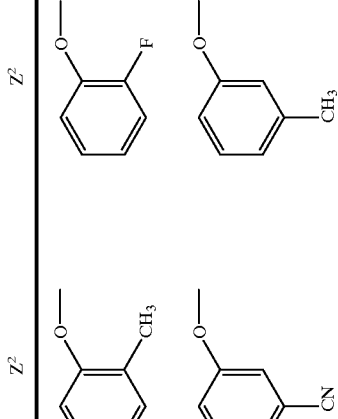
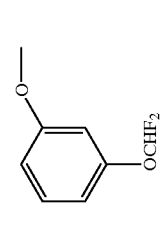
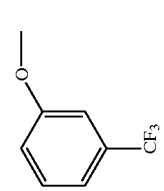
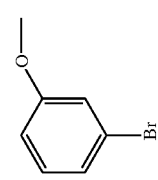
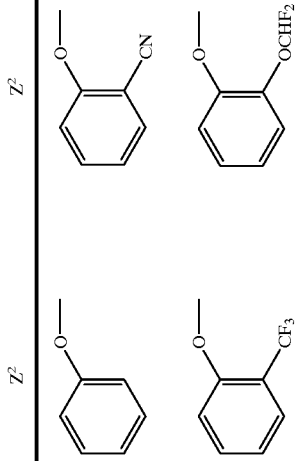
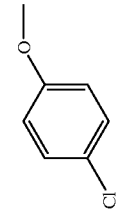

TABLE 8-continued
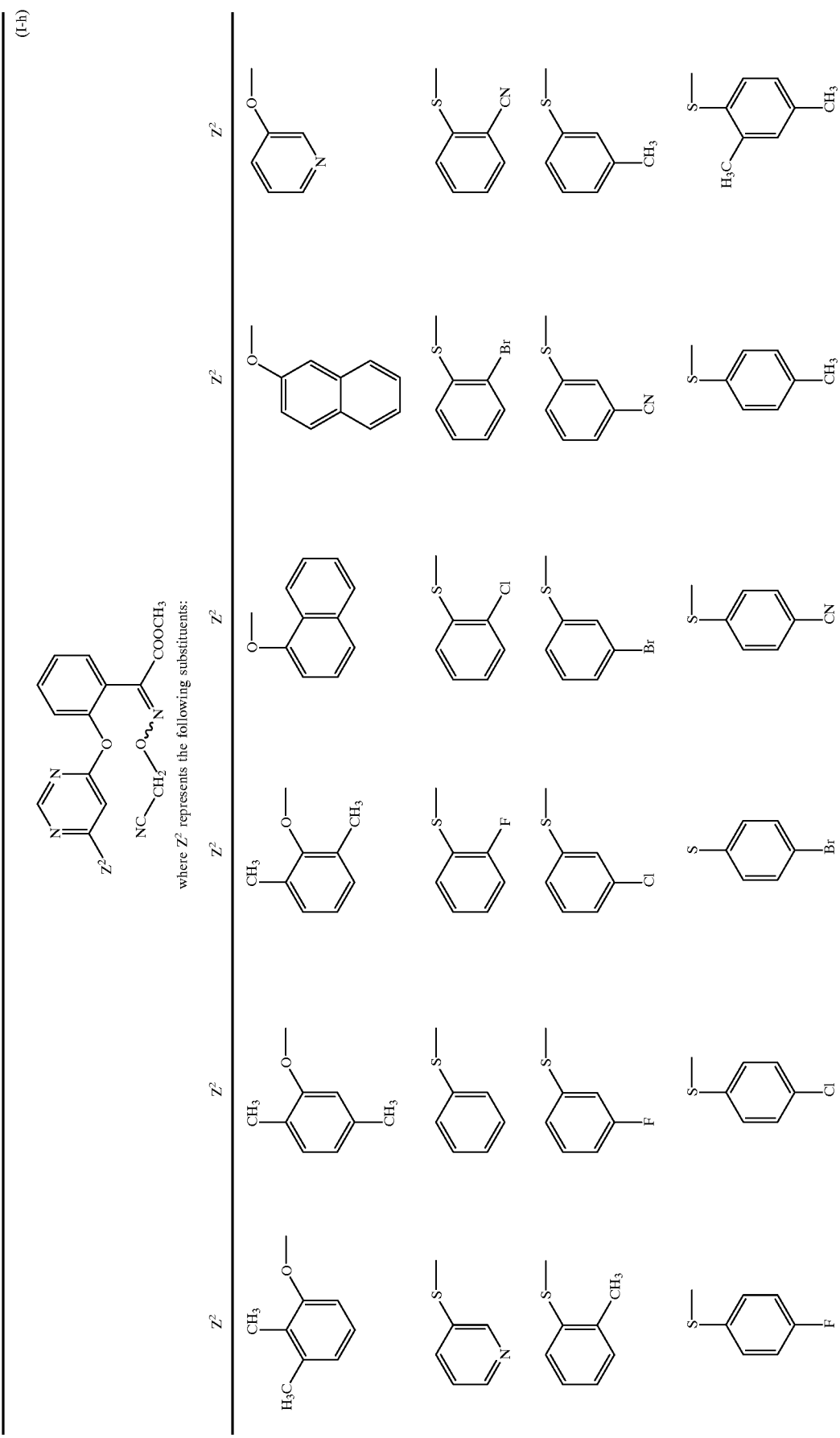

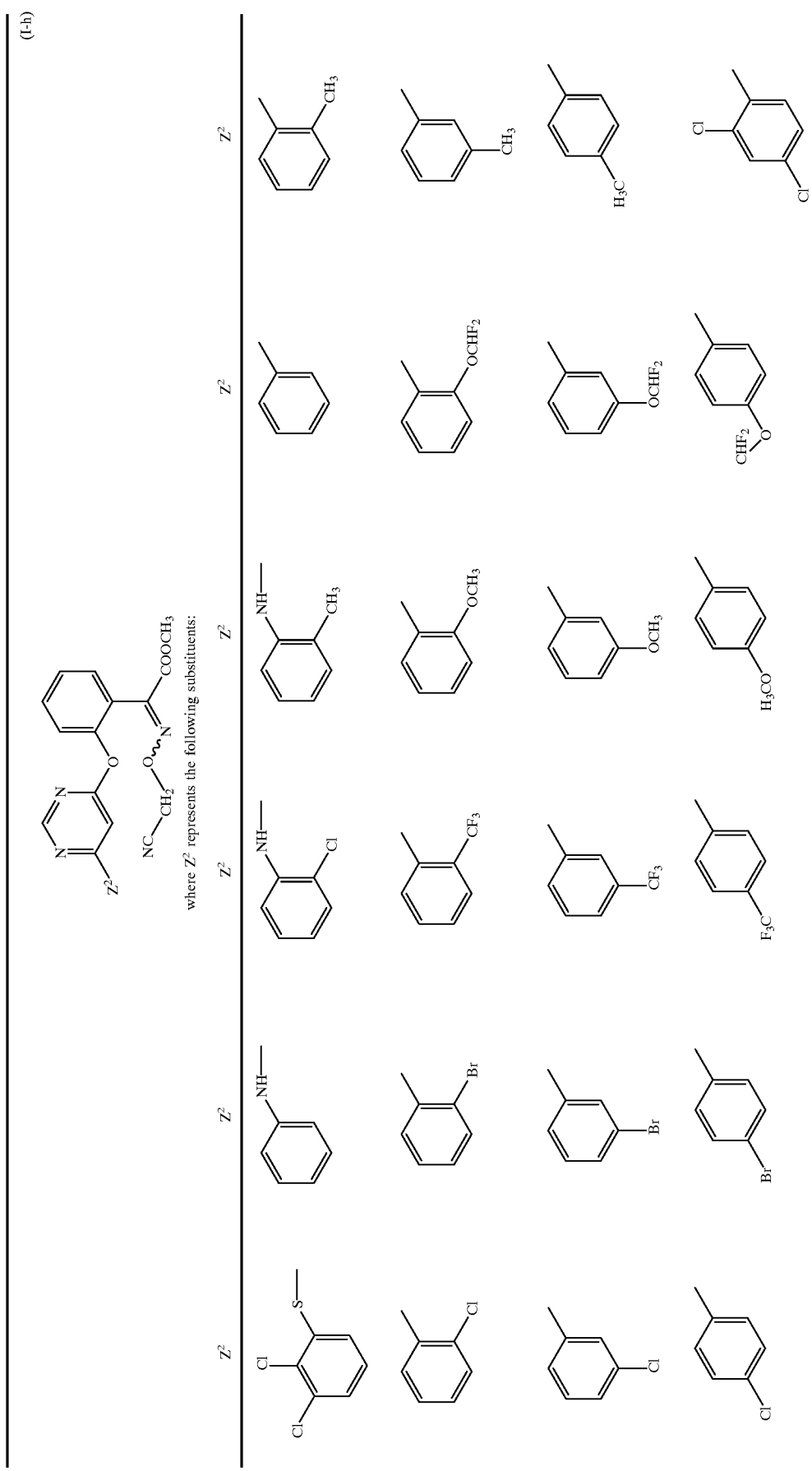

TABLE 8-continued
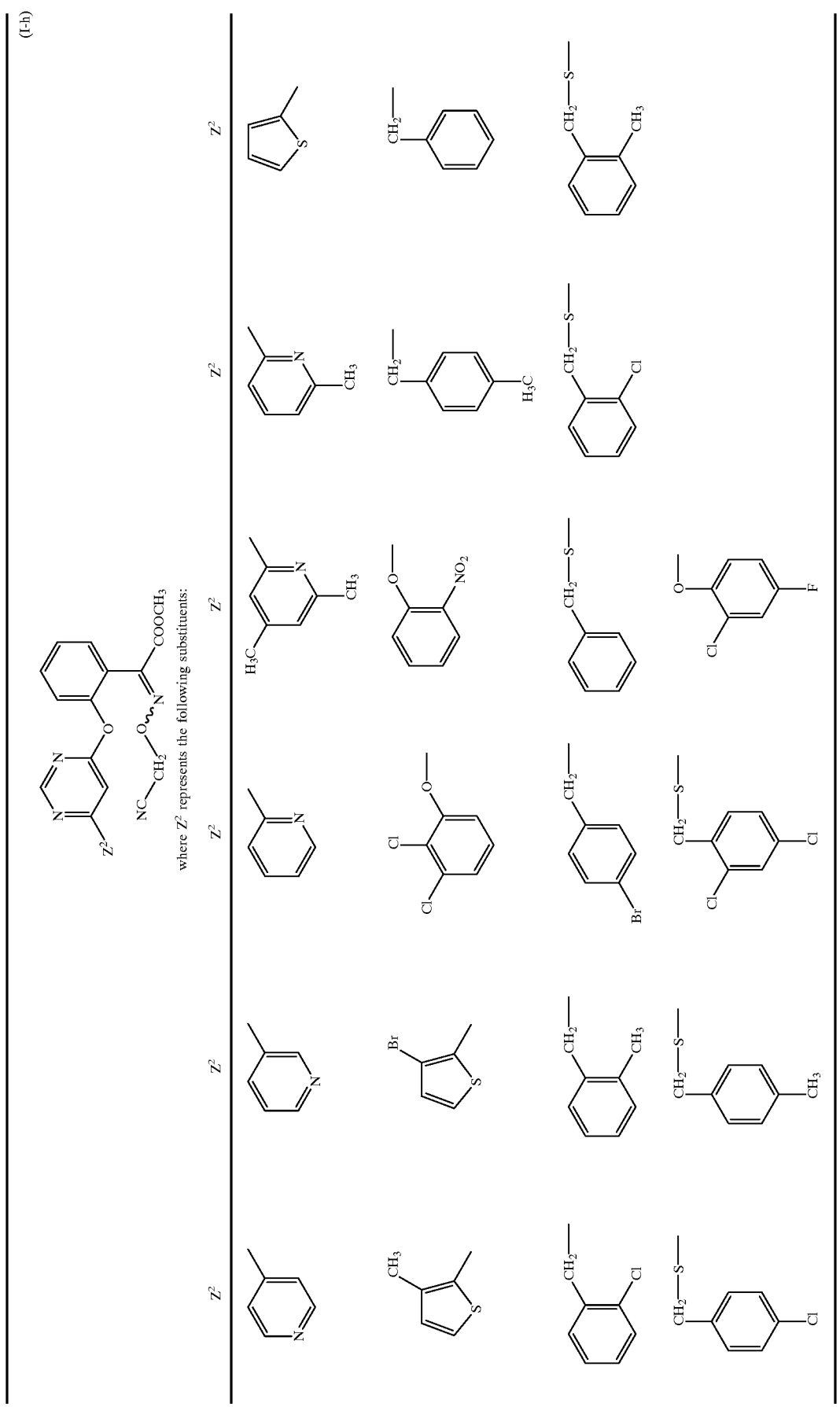

TABLE 9
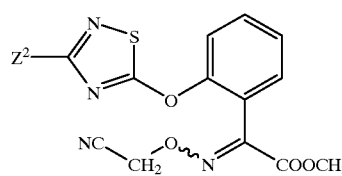
(I-i)
where $Z^2$ represents the substituents listed in Table 8.
TABLE 10
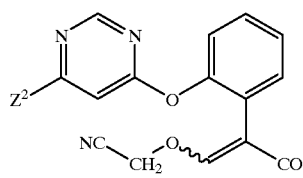
(I-j)
where $Z^2$ represents the substituents listed in Table 8.
TABLE 11
(I-k)
where $Z^2$ represents the substituents listed in Table 8.
TABLE 12
(I-l)
where $Z^3$ represents the following substituents:

TABLE 12
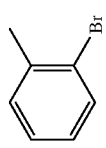

TABLE 12-continued
| $Z^3$ | $Z^3$ | $Z^3$ | $Z^3$ | $Z^3$ | $Z^3$ |
|---|---|---|---|---|---|
| 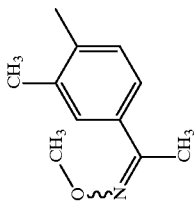 | 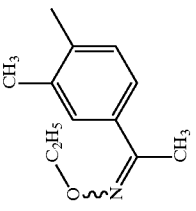 | 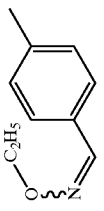 | | | |
| 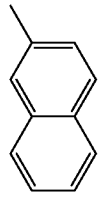 | 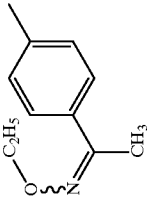 | 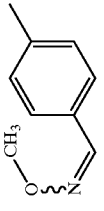 | | | |
| 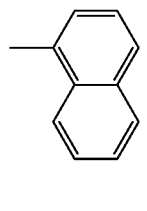 | 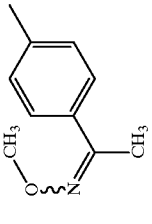 | 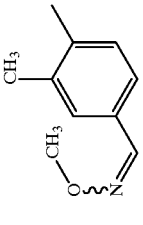 | | | |
| | | 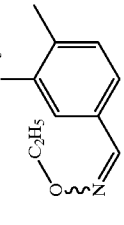 | | | |

TABLE 13

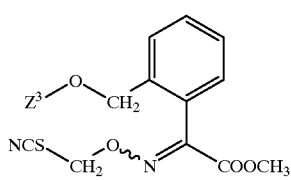

(I-m)

where $Z^3$ represents the substituents listed in Table 11.

TABLE 14

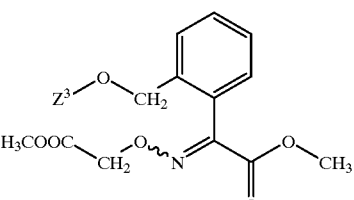

(I-n)

where $Z^3$ represents the substituents listed in Table 11.

TABLE 15

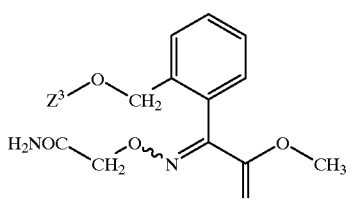

(I-o)

where $Z^3$ represents the substituents listed in Table 11.

TABLE 16

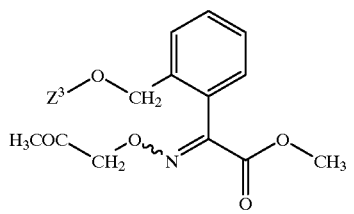

(I-p)

where $Z^3$ represents the substituents listed in Table 11.

The formula (II) provides a general definition of the hydroxy compounds required as starting materials for carrying out the process a) according to the invention. In this formula (II), Ar, E, G, $R^1$ and Z each preferably or in particular have those meanings which have already been indicated in connection with the description of the compounds of the formula (I) according to the invention as being preferred or particularly preferred for Ar, E, G, $R^1$ and Z.

The starting materials of the formula (II) are known and/or can be prepared by processes known per se (cf. for example, EP-A 554767).

The formula (III) provides a general definition of the halogen compounds furthermore required as starting materials for carrying out the process a) according to the invention. In the formula (III), $R^2$ preferably or in particular has that meaning which has already been indicated in connection with the description of the compounds of the formula (I) according to the invention as being preferred or particularly preferred for $R^2$. $X^1$ represents halogen, preferably chlorine or bromine.

The halogen compounds of the general formula (III) are known reagents of organic chemistry.

The formula (IV) provides a general definition of the hydroxyaryl compounds required as starting materials for carrying out the process b) according to the invention. In this formula (IV), Ar, E, $R^1$ and $R^2$ each preferably or in particular have those meanings which have already been indicated in connection with the description of the compounds of the formula (IV) according to the invention as being preferred or particularly preferred for Ar, E, $R^1$ and $R^2$.

The hydroxyaryl compounds of the formula (IV) have not been disclosed; as novel compounds, they form part of the subject matter of the present application.

The hydroxyaryl compounds of the formula (IV) are obtained (process c) when tetrahydropyranyl ethers of the formula (VI)

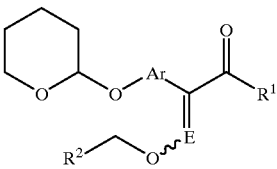

(VI)

in which

Ar, E, $R^1$ and $R^2$ are each as defined above are hydrolyzed, if appropriate in the presence of a diluent, preferably in aliphatic, alicyclic or aromatic hydrocarbons such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an ester such as methyl acetate or ethyl acetate; a sulphoxide such as dimethyl sulphoxide; a sulphone such as sulpholane; an alcohol such as methanol, ethanol, n- or i-propanol, n-, i-, sec- or tert-butanol, ethanediol, propane- 1,2-diol, ethoxyethanol, methoxyethanol, diethylene glycol monomethyl ether, diethylene glycol monoethyl ether, mixtures thereof with water or pure water and, if appropriate, in the presence of an acid, preferably an inorganic or organic protic or Lewis acid such as, for example, hydrogen chloride, sulphuric acid, phosphoric acid, formic acid, acetic acid, trifluoroacetic acid, methanesulphonic acid, trifluoromethanesulphonic acid, toluenesulphonic acid, boron trifluoride (also as etherate), boron tribromide, aluminium trichloride, zinc chloride, iron(III) chloride, antimony pentachloride, or else a polymeric acid such as, for example, an acid ion exchanger, an acidic alumina or acidic silica gel, at temperatures from −20° C. to 120° C., preferably at temperatures from −10° C. to 80° C.

The formula (VI) provides a general definition of the tetrahydropyranyl ethers required as starting materials for carrying out the process c) according to the invention. In this formula (VI), Ar, E, $R^1$ and $R^2$ each preferably or in particular have those meanings which have already been indicated in connection with the description of the compounds of the formula (I) according to the invention as being preferred or particularly preferred for Ar, E, $R^1$ and $R^2$.

The tetrahydropyranyl ethers of the formula (VI) have not been disclosed; as novel compounds they form part of the subject matter of the present application.

The tetrahydropyranyl ethers of the formula (VI) are obtained (process d1) when arylacetic acid derivatives of the formula (VII)

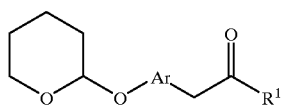

(VII)

in which

Ar and $R^1$ are as defined above are initially reacted with a formic acid derivative such as, for example, methyl formate, carbon monoxide, a dialkylformamide acetal or a bis-dialkylaminoalkoxymethane, if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an ester such as methyl acetate or ethyl acetate; an amide such as N,N-dimethylformamide, N,N-dimethylacetamide, N-methylformanilide, N-methylpyrrolidone or hexamethylphosphoric triamide; a sulphoxide such as dimethyl sulphoxide; a sulphone such as sulpholane; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether, and, if appropriate, in the presence of a basic catalyst, preferably an alkaline earth metal or alkali metal hydride, hydroxide, amide, alkoxide, acetate, carbonate or bicarbonate such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from −20° C. to 120° C., preferably at temperatures from −10° C. to 80° C., and the resulting enols of the formula (VIII)

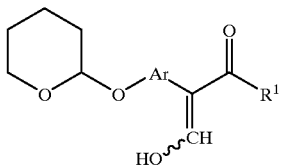

(VIII)

in which

Rr and $R^1$ are each as defined above are reacted, preferably without any further work-up, with a halogen compound of the formula (III) already described above, if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an ester such as methyl acetate or ethyl acetate; an amide such as N,N-dimethylformamide, N,N-dimethylacetamide, N-methylformanilide, N-methylpyrrolidone or hexamethylphosphoric triamide; a sulphoxide such as dimethyl sulphoxide; a sulphone such as sulpholane; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether, mixtures thereof with water or pure water, and, if appropriate, in the presence of a base, preferably an alkaline earth metal or alkali metal hydride, hydroxide, amide, alkoxide, acetate, carbonate or bicarbonate such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from −20° C. to 120° C., preferably at temperatures from −10° C. to 80° C., or when (process d2) the abovementioned arylacetic acid derivatives of the formula (VII) are reacted with an alkali metal nitrite such as, for example, sodium nitrite, or preferably an alkyl nitrite such as, for example, t-butyl nitrite or t-amyl nitrite, if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an ester such as methyl acetate or ethyl acetate; an amide such as N,N-dimethylformamide, N,N-dimethylacetamide, N-methylformanilide, N-methylpyrrolidone or hexamethylphosphoric triamide; a sulphoxide such as dimethyl sulphoxide; a sulphone such as sulpholane; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether, and, if appropriate, in the presence of a base, preferably an alkaline earth metal or alkali metal hydride, hydroxide, amide, alkoxide, acetate, carbonate or bicarbonate such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from −50° C. to 100° C., preferably at temperatures from −20° C. to 50° C., and the resulting oximes of the formula (IX)

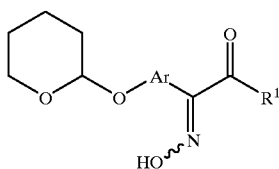

(IX)

in which

Ar and $R^1$ are each as defined above are reacted, preferably without any further work-up, with a halogen compound of the formula (III) already described above, if appropriate in the presence of a diluent, preferably an aliphatic, alicyclic or aromatic hydrocarbon such as, for example, petroleum ether, hexane, heptane, cyclohexane, methylcyclohexane, benzene, toluene, xylene or decalin; a halogenated hydrocarbon such as, for example, chlorobenzene, dichlorobenzene, dichloromethane, chloroform, carbon tetrachloride, dichloroethane or trichloroethane; an ether such as diethyl ether, diisopropyl ether, methyl t-butyl ether, methyl t-amyl ether, dioxane, tetrahydrofuran, 1,2-dimethoxyethane, 1,2-diethoxyethane or anisole; a ketone such as acetone, butanone, methyl isobutyl ketone or cyclohexanone; a nitrile such as acetonitrile, propionitrile, n- or i-butyronitrile or benzonitrile; an ester such as methyl acetate or ethyl acetate; an amide such as N,N-dimethylformamide, N,N-dimethylacetamide, N-methylformanilide, N-methylpyrrolidone or hexamethylphosphoric triamide; a sulphoxide such as dimethyl sulphoxide; a sulphone such as sulpholane; an alcohol such as methanol, ethanol, n- or i-propanol, n-, i-, sec- or tert-butanol, ethanediol, propane-1,2-diol, ethoxyethanol, methoxyethanol, diethylene glycol monomethyl ether or diethylene glycol monoethyl ether, mixtures thereof with water or pure water, and, if appropriate, in the presence of a base, preferably an alkaline earth metal or alkali metal hydride, hydroxide, amide, alkoxide, acetate, carbonate or bicarbonate such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, or a tertiary amine such as trimethylamine, triethylamine, tributylamine, N,N-dimethylaniline, N,N-dimethyl-benzylamine, pyridine, N-methylpiperidine, N-methylmorpholine, N,N-dimethylaminopyridine, diazabicyclooctane (DABCO), diazabicyclononene (DBN) or diazabicycloundecene (DBU), at temperatures from −20° C. to 120° C., preferably at temperatures from −10° C. to 80° C.

The formula (VII) provides a general definition of the arylacetic acid derivatives required as starting materials for carrying out the processes d1) and d2) according to the invention for preparing the tetrahydropyranyl ethers of the formula (VI). In this formula (VII), Ar and $R^1$ each preferably or in particular have those meanings which have already been indicated in connection with the description of the compounds of the formula (I) according to the invention as being preferred or particularly preferred for Ar and $R^1$.

The arylacetic acid derivatives of the formula (VII) are known and/or can be prepared by known processes (cf. for example J. Org. Chem. 1994, 203–13).

The formula (V) provides a general definition of the aryl compounds furthermore required as starting materials for carrying out the process b) according to the invention. In this formula (V), $Ar^1$ preferably or in particular has that meaning which has already been indicated in connection with the description of the compounds of the formula (I) according to the invention as being preferred or particularly preferred for $Ar^1$. V represents halogen, preferably fluorine or chlorine, or represents Z—T—, where Z and T preferably or in particular have those meanings which have already been indicated in connection with the description of the compounds of the formula (I) according to the invention as being preferred or particularly preferred for Z and T. $X^2$ represents halogen, preferably fluorine or chlorine, or represents alkylsulphonyl or arylsulphonyl, preferably methylsulphonyl, benzylsulphonyl or tolylsulphonyl.

The aryl compounds of the formula (V) are known chemicals for synthesis and/or can be prepared by known processes (cf. for example J. Org. Chem. 1994, 203–13, J. Heterocyclic Chem. 1993, 357 and Khim.-Farm. Zh. (1989), 23(6), 705–7).

Suitable diluents for carrying out the processes a) and b) according to the invention are all inert organic solvents. These preferably include aliphatic, alicyclic or aromatic hydrocarbons such as, for example, petroleum ether, hexane, heptane, cyclohexane, methylcyclohexane, benzene, toluene, xylene or decalin; halogenated hydrocarbons such as, for example, chlorobenzene, dichlorobenzene, dichloromethane, chloroform, carbon tetrachloride, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-di-methylacetamide, N-methylformanilide, N-methylpyrrolidone or hexamethylphosphoric triamide; esters such as methyl acetate or ethyl acetate; sulphoxides such as dimethyl sulphoxide; sulphones such as sulpholane; alcohols such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

If appropriate, the processes a) and b) according to the invention are carried out in the presence of a suitable acid acceptor. Suitable acid acceptors are all customary inorganic or organic bases. These include, for example, alkaline earth metal or alkali metal hydrides, hydroxides, amides, alkoxides, acetates, carbonates or bicarbonates such as, for example, sodium hydride, sodium amide, sodium methoxide, sodium ethoxide, potassium tert-butoxide, sodium hydroxide, potassium hydroxide, ammonium hydroxide, ammonium acetate, potassium acetate, calcium acetate, ammonium acetate, sodium carbonate, potassium carbonate, potassium bicarbonate, sodium bicarbonate or ammonium carbonate, and tertiary amines such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process a) and b) according to the invention, the reaction temperatures may be varied over a relatively wide range. In general, temperatures from 0° C. to 150° C., preferably temperatures from 0° C. to 80° C., are employed.

The process a) according to the invention for preparing the compounds of the formula (I) is carried out by employing generally 1 to 15 mol, preferably 1 to 8 mol, of halogen compound of the formula (III) per mole of the hydroxyl compound of the formula (II).

The process b) according to the invention for preparing the compounds of the formula (I) is carried out by employing generally 0.2 to 5 mol, preferably 0.5 to 2 mol, of aryl compound of the general formula (V) per mole of the hydroxyaryl compounds of the general formula (IV).

The processes a) and b) according to the invention are generally carried out at atmospheric pressure. However, it is also possible to work at elevated or reduced pressure—in general between 0.1 bar and 10 bar.

The reactions are carried out and the reaction products are worked up and isolated according to known methods (cf. also the Preparation Examples).

The active compounds according to the invention have strong microbicidal activity and are employed in practice for controlling undesirable microorganisms. The active compounds are suitable for use as crop protection agents, in particular as fungicides.

Fungicides are employed in crop protection for controlling Plasmodiophoromycetes, Oomycetes, Chytridiomycetes, Zygomycetes, Ascomycetes, Basidiomycetes and Deuteromycetes.

Some pathogens causing fungal diseases which come under the generic names listed above may be mentioned as examples, but not by way of limitation:

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubense;*

Plasmopara species, such as, for example, *Plasmopara viticola;*

Peronospora species, such as, for example, *Peronospora pisi* or *Peronospora brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *Pyrenophora graminea* (conidiae form: Drechslera, synonym: Helminthosporium);

Cochliobolus species, such as, for example, *Cochliobolus sativus* (conidiae form: Drechslera, synonym: Helminthosporium);

Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptosphaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds according to the invention can be employed particularly successfully for controlling cereal diseases, for example against Erysiphe species, Leptosphaeria and Pyrenophora species or diseases in viticulture, fruit-growing and vegetable-growing, for example against Podosphera species, or else rice diseases, for example against Pyricularia species. The active compounds according to the invention additionally have particularly strong and wide-ranging in vitro activity.

Depending on their particular physical and/or chemical properties, the active compounds can be converted, if desired, into customary formulations, such as solutions, emulsions, suspensions, powders, foams, pastes, granules, aerosols and microencapsulations in polymeric substances and in coating compositions for seeds, and ULV cold and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to use for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatc hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water; liquefied gaseous extenders or carriers are to be understood as meaning liquids which are gaseous at ambient temperature and under atmospheric pressure, for example aerosol propellants such as halogenated hydrocarbons, or else butane, propane, nitrogen and carbon dioxide; suitable solid carriers are: for example, ground natural minerals such as kaolins, clays, talc, chalk, quartz, attapulgite, montmorillonite or diatomaceous earth, and ground synthetic minerals such as finely divided silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or, in their formulations, also as a mixture with known fungicides, bactericides, acaricides, nematicides or insecticides in order thus, for example, to widen the spectrum of action or to prevent development of resistance.

In many cases, synergistic effects are achieved.

Examples of co-components in mixtures are the following compounds:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl) benzamide; (E)-2-methoxyimino-N-methyl-2-(2-phenoxyphenyl)acetamide; 8-hydroxyquinoline sulphate; methyl (E)-2-{2-[6-(2-cyano-phenoxy)pyrimidin-4yloxy]phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cypro-conazole, cyprofuram, dichlorophen, diclobutrazol, diclofluanid, diclomezine, dicloran, diethofencarb, difenoconazole, dimethirimol, dimethomorph, diniconazole, dinocap, diphenylamine, dipyrithione, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracycline, probenazole, streptomycin, tecloftalam, copper sulphate and other copper preparations.

Isecticides/Acaricides/Nematicides abamectin, abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157419, CGA 184699, chloethocarb, chlorethoxyfos, chloretoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton—S—methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lamda-cyhalothrin, lufenuron, malathion, mecarbam, mervinphos, mesulfenfos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, ,primiphos A, profenofos, profenophos, promecarb, propaphos, propoxur, prothiofos, prothiophos, prothoate, pymetrozin, pyrachlophos, pyraclofos, pyraclophos, pyradaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathene, triazophos, triazuron, trichlorfon, triflumuron, trimethacarb, vamidothion, XMC, xylylcarb, YI 5301/5302, zetamethrin.

It is also possible to mix the active compounds according to the invention with other known active compounds, such as herbicides, or fertilizers and growth regulators.

The active compounds can be used as such or in the form of their formulations or the use forms prepared therefrom, such as ready-to-use solutions, suspensions, wettable powders, pastes, soluble powders, dusts and granules. They are used in the customary manner, for example by wetting, spraying, atomizing, scattering, dusting, foaming, brushing on and the like. It is further possible to apply the active compounds by the ultra-low volume method or to inject the active compound formulation, or the active compound itself, into the soil. The seed of the plants can also be treated.

In the treatment of parts of plants, the active compound concentrations in the use forms can be varied within a substantial range: They are, in general, between 1 and 0.0001% by weight, preferably between 0.5 and 0.001% by weight.

In the treatment of seed, amounts of active compound of from 0.001 to 50 g, preferably 0.01 to 10 g, are generally required per kilogram of seed.

In the treatment of the soil, active compound concentrations of from 0.00001 to 0.1% by weight, preferably from 0.0001 to 0.02% by weight, are required at the site of action.

PREPARATION EXAMPLES

Example 1

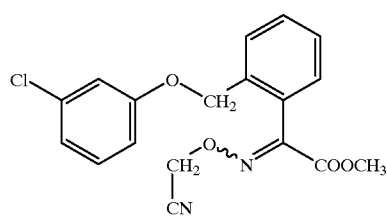

Process a)

With stirring, 0.67 g (0.006 mol) of potassium t-butoxide and 0.35 g (0.0055 mol) of chloroacetonitrile are added successively to a solution of 1.6 g (0.005 mol) of 2-hydroximino-2-[2-(3-chlorophenoxymethyl)-phenyl]-acetamide in 50 ml of tetrahydrofuran, and the mixture is stirred at 20° C. for 2 hours. The mixture is heated to boiling point for a short while and then, without any further heating, stirred for a further 18 hours. The mixture is subsequently poured into water and extracted with methyl t-butyl ether. The organic phase is dried over magnesium sulphate, filtered and concentrated under reduced pressure. The residue is stirred with diisopropyl ether and filtered with suction. 1.1 g (61.4% of theory) of 2-cyanomethoximino-2-[2-(2-methylphenoxy-methyl)-phenyl]-acetamide are obtained.

$^1$H NMR (CDCl$_3$, TMS): δ=3.84 (s, 3H); 4.81 (s, 2H); 4.96 (s, 2H) ppm

Example 2

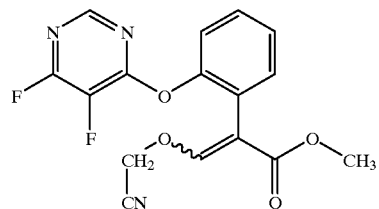

Process b)

1.74 g (13 mmol) of 4,5,6-trifluoropyrimidine and 0.43 g (14.3 mmol) of 80 % strength sodium hydride suspension are added to a solution of 3 g (13 mmol) of methyl 2-(2-hydroxyphenyl)-3-cyanomethoxy-acrylate in 50 ml of dimethylformamide which has been cooled to −10° C. The mixture is stirred without any further cooling, and within an hour it warms to 20° C. The solution is stirred at 20° C. for a further 2 hours, poured into 100 ml of water and extracted twice with 150 ml of methyl t-butyl ether each time. The combined organic phases are dried over sodium sulphate and concentrated under reduced pressure. 4.4 g (97.8% of theory) of methyl (2-[2-(5,6-trifluoropyrimid-4-yloxy)-phenyl]-3-cyanomethoxy-acrylate are obtained.

$^1$H NMR (CDCl$_3$, TMS): δ=3.67 (s, 3H), 4.63 (s, 2H).

Example 3

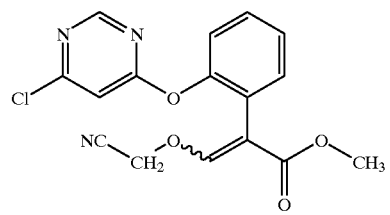

Process b) 1.94 g (13 mmol) of 4,6-dichloropyrimidine and 0.43 g (14.3 mmol) of 80% strength sodium hydride suspension are added to a solution of 3 g (13 mmol) of methyl 2-(2-hydroxyphenyl)-3-cyanomethoxy-acrylate in 50 ml of dimethylformamide which has been cooled to −10° C. The mixture is stirred without any further cooling, and within an hour it warms to 20° C. The solution is stirred at 20° C. for a further 2 hours, poured into 100 ml of water and extracted twice with 150 ml of methyl t-butyl ether each time. The combined organic phases are dried over sodium sulphate and concentrated under reduced pressure. 3.9 g (86.7% of theory) of methyl (2-[2-(6-chloropyrimid4-yloxy)-phenyl]-3-cyanomethoxy-acrylate are obtained.

$^1$H NMR (CDCl$_3$, TMS): δ=3.64 (s, 3H), 4.61 (s, 2H).

Preparation of the Starting Material

Example (IV-1)

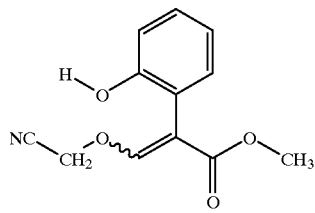

Process c)

A solution of 14.4 g (45.3 mmol) of methyl 2-[2-(tetrahydropyran-2-yloxy)-phenyl]-3-cyanomethoxy-acrylate in 50 ml of methanol is admixed with 5 g of acidic ion exchanger and stirred at 20° C. for 3 hours. The ion exchanger is filtered off and the filtrate is concentrated under reduced pressure. The residue is chromatographed over silica gel using dichloromethane/ethyl acetate (10:1). 7.8 g (74% of theory) of methyl 2-(2-hydroxyphenyl)-3-cyanomethoxy-acrylate are obtained.

$^1$H NMR (CDCl$_3$, TMS): δ=3.80 (s, 3H), 4.63 (s, 2H).

Preparation of the Precursor

Example (VI-1)

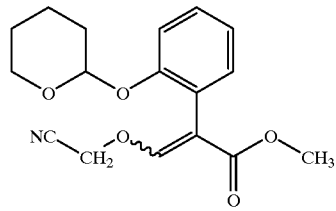

Process d1)

At 20° C., a solution of 15 g (60 mmol) of methyl 2-[2-(tetrahydropyran-2-yloxy)phenyl]-acrylate in 36 ml of methyl formate is added dropwise to a suspension of 1.96 g (66 mmol) of sodium hydride (80% strength) in 50 ml of dimethylformamide. After 4 hours, 15 g of potassium carbonate and 9 g of chloroacetonitrile are added to this mixture, which is stirred at 20° C. for a further 14 hours and then poured into water. The reaction mixture is extracted with ethyl acetate and the organic phase is dried over sodium sulphate and concentrated under reduced pressure. 15.9 g (83.55% of theory) of methyl 2-[2-(tetrahydropyran-2-yloxy)-phenyl]-3-cyanomethoxy-acrylate are obtained.

$^1$H NMR (CDCl$_3$, TMS): δ=3.72 (s, 3H), 4.63 (s, 2H), 5.42 (m, 1H).

Example 4

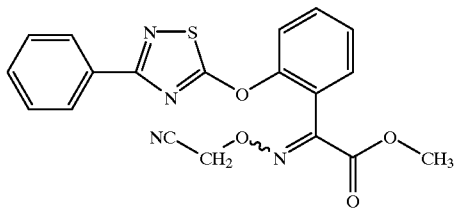

Process b)

0.2 g (6 mmol) of an 80% strength sodium hydride suspension is added to a solution of 1.4 (6 mmol) of methyl 2-(2-hydroxyphenyl)-2-cyanomethoximino-acetate and 1.9 g (6 mmol) of 3-phenyl-5-(4-tolylsulphonyl)-1,2,4-thiadiazole in 20 ml of dimethylformamide which has been cooled to 0° C., and the mixture is stirred without any further cooling for 48 hours. The reaction mixture is taken up in ethyl acetate, washed with water, dried over sodium sulphate and concentrated under reduced pressure. 0.8 g (34% of theory) of methyl 2-[2-(3-phenyl-1,2,4thiadiazol-5-yloxy)-phenyl]-2-cyanomethoximino-acetate is obtained.

$^1$H NMR (CDCl$_3$, TMS): δ=3.80 (s, 3H), 4.80 (s, 2H).

Preparation of the Starting Material

Example (IV-2)

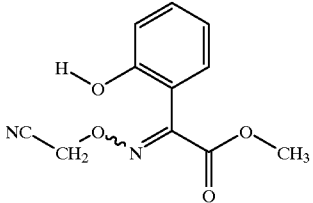

Process c)

A solution of 3.2 g (10 mmol) of methyl 2-[2-(tetrahydropyran-2-yloxy)-phenyl]-2-cyanomethoximino-acetate in 20 ml of methanol is mixed with 0.1 g of acidic ion exchanger and stirred at 20° C. for 18 hours. The ion exchanger is filtered off and the filtrate is concentrated under reduced pressure. The residue is chromatographed over silica gel using hexane/acetone (7:3). 1.4 g (60% of theory) of methyl 2-(2-hydroxyphenyl)-2-cyanomethoximino-acetate are obtained.

$^1$H NMR (CDCl$_3$, TMS): δ=3.95 (s, 3H), 4.90 (s, 2H).

Preparation of the Precursor

Example (VI-2)

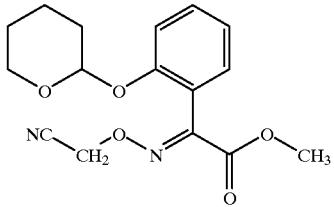

Process d2)

A solution of 34.3 g (300 mmol) of t-butyl nitrite and 25 g (100 mmol) of methyl 2-[2-(tetrahydropyran-2-yloxy)- phenyl]-acrylate in 30 ml of t-butanol is added dropwise to a solution of 12.3 g (110 mmol) of potassium t-butoxide in 120 ml of t-butanol, and the reaction solution warms to 45° C. After 2 hours, 13.2 g (110 mmol) of bromoacetonitrile are added to this mixture and stirring is continued at 20° C. for a further 18 hours. The reaction mixture is concentrated under reduced pressure, taken up in methyl t-butyl ether, washed with water, dried over sodium sulphate and concentrated under reduced pressure. The residue is chromatographed over silica gel using hexane/acetone (8:2). 14.9 g (46.9% of theory) of methyl 2-[2-(tetrahydropyran-2-yloxy)-phenyl]-3-cyanomethoxy-acrylate are obtained.

$^1$H NMR (CDCl$_3$, TMS): δ=3.9 (s, 3H), 4.85 (s, 2H).

Similarly to Examples (1–4), and in accordance with the general description of the preparation process according to the invention, the compounds of the formula (I) according to the invention listed in Table 17 below are additionally obtained:

TABLE 17

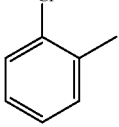

(I)

| Ex. No. | Z | G | Ar | E | R$^1$ | R$^2$ | physical constants |
|---|---|---|---|---|---|---|---|
| 5 | 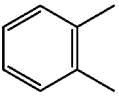 | —O—CH$_2$— | 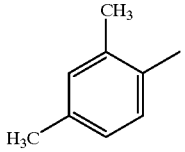 | N | —OCH$_3$ | —CN | $^1$H NMR*): 3.86(s). 4.82(s). 5.03(s) |
| 6 | 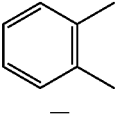 | —O—CH$_2$— | 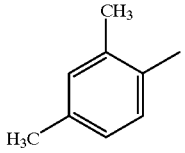 | N | —OCH$_3$ | —CN | $^1$H NMR*): 3.80(s), 3.89(s). (isomer mixture) |
| 7 | 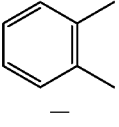 | —O—CH$_2$— | 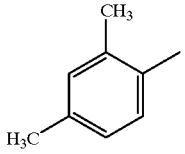 | N | —OCH$_3$ | —CN | $^1$H NMR*): 3.89(s), 4.73(s). (Z-isomer) |
| 8 | 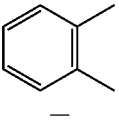 | —O—CH$_2$— | 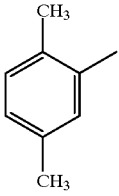 | N | —OCH$_3$ | —CN | $^1$H NMR*): 3.80(s), 4.77(s). (E-isomer) |
| 9 | 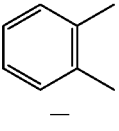 | —O—CH$_2$— | 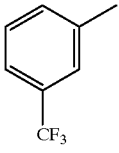 | N | —OCH$_3$ | —CN | $^1$H NMR*): 3.81(s), 4.79(s), 4.55(s). |
| 10 | 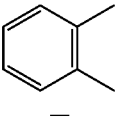 | —O—CH$_2$— | | N | —OCH$_3$ | —CN | $^1$H NMR*): 3.85(s), 4.82(s), 4.95(s). |

TABLE 17-continued
(I)
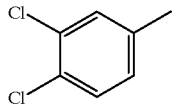
| Ex. No. | Z | G | Ar | E | R¹ | R² | physical constants |
|---|---|---|---|---|---|---|---|
| 11 | 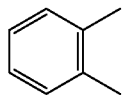 | —O—CH₂— | 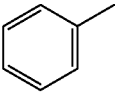 | N | —OCH₃ | —CN | ¹H NMR*): 3.83(s), 4.80(s), 5.01(s). |
| 12 | 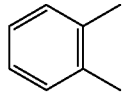 | —O—CH₂— | 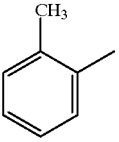 | N | —OCH₃ | —CN | ¹H NMR*): 3.81(s), 4.76(s), 4.98(s). |
| 13 | 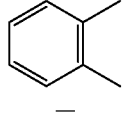 | —O—CH₂— | 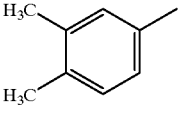 | N | —OCH₃ | —CN | ¹H NMR*): 2.23(s), 3.80(s), 4.99(s). |
| 14 | 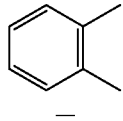 | —O—CH₂— | 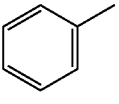 | N | —OCH₃ | —CN | ¹H NMR*): 3.82(s), 4.78(s), 4.93(s). |
| 15 | 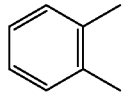 | —O—CH₂— | 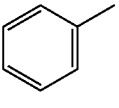 | N | —OCH₃ | —SCN | ¹H NMR*): 3.82(s), 5.03(s), 5.54(s). |
| 16 | 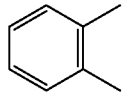 | —O—CH₂— | 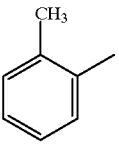 | N | —OCH₃ | —COOCH₃ | ¹H NMR*): 3.72(s), 3.80(s), 4.75(s). |
| 17 | 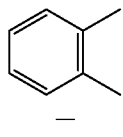 | —O—CH₂— | 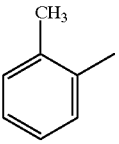 | N | —OCH₃ | —SCN | ¹H NMR*): 3.79(s), 5.03(s), 5.54(s). |
| 18 | 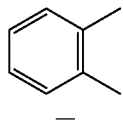 | —O—CH₂— | | N | —OCH₃ | —COOCH₃ | ¹H NMR*): 3.73(s), 3.79(s), 4.76(s). |

TABLE 17-continued

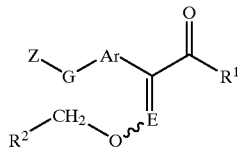

| Ex. No. | Z | G | Ar | E | R¹ | R² | physical constants |
|---|---|---|---|---|---|---|---|
| 19 | 3-Cl-phenyl | —O—CH₂— | 2-methylphenyl | N | —OCH₃ | —COOCH₃ | ¹H NMR*): 3.74(s), 4.77(s), 5.10(s). |

*) The ¹H NMR spectra were recorded in deuterochloroform (CDCl₃) or hexadeuterodimethyl sulphoxide (DMSO-d₆) using tetramethylsilane (TMS) as internal standard. The chemical shift is stated as δ value in ppm.

Use Examples

In the use examples below, the compound shown below is used as comparative substance:

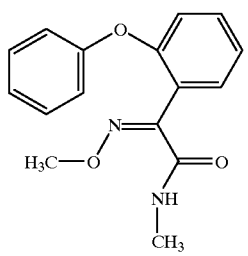

(A)

(E)-alpha-(methoxyimino)-N-methyl-2-phenoxy-benzeneacetamide

Example A

Podosphaera Test (Apple)/Protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew moist. After the spray coating has dried on, the plants are inoculated by dusting with conidia of the causative organism (*Podosphaera leucotricha*) of apple mildew.

The plants are then placed in a greenhouse at 23° C. and a relative atmospheric humidity of about 70%.

Evaluation is carried out 10 days after the inoculation.

In this test, for example the following compounds of Preparation Examples (6), (7), (8) and (9) exhibit, at an active compound concentration of 100 ppm, an efficacy of 82 to 99%.

Example B

*leptosphaeia nodorum* test (Wheat)/Curative

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for curative activity, young plants are sprayed with a suspension of spores of *Leptosphaeria nodorum*. The plants remain in an incubation chamber at 20° C. and 100% relative atmospheric humidity for 48 hours. The plants are then sprayed with the preparation of active compound at the stated application rate.

The plants are placed in a greenhouse at a temperature of about 15° C. and a relative atmospheric humidity of about 80%.

Evaluation is carried out 10 days after the inoculation.

In this test, for example the following compounds of Preparation Examples (7), (8) and (9) exhibit, at an active compound application rate of 125 g/ha, an efficacy of 50%.

We claim:

1. Compounds of the formula (I)

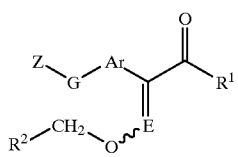

(I)

in which

Ar represents optionally substituted arylene,

E represents =CH— or nitrogen,

G represents a single bond, represents oxygen, sulphur or represents respectively optionally halogen-, hydroxyl-, alkyl-, halogenoalkyl- or cycloalkyl-substituted alkanediyl, alkenediyl, alkinediyl or one of the groupings below —Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N=N—, —S(O)ₙ—, —CH₂—S(O)ₙ—, —CQ—, —S(O)ₙ—CH₂—, —C(R³)=N—O—, —C(R³)=N—O—CH₂—, —N(R⁴)—, —CQ—N(R⁴)—, —N(R⁴)—CQ—, —Q—CQ—N(R⁴)—, —N=C(R³)—Q—CH₂—, —CH₂—O—N=C(R³)—, —C(CH₃)—O—

N=C(R³)—, —N(R⁴)—CQ—Q—, —CQ—N(R⁴)—CQ—Q—, —N(R⁴)—CQ—Q—CH₂—, —Q—C(R³)=N—O—CH₂—, —N(R⁴)—C(R³)=N—O—CH₂—, —O—CH₂—C(R³)=N—O—CH₂—, —N=N—C(R³)=N—O—CH₂—, —C(=N—O—R⁵)—C(R³)=N—OCH₂—, —C(=N—O—R⁵)—C(R³)—O—N=CH—, —C(=N—O—R⁵)—C(R³)—O—N=C(CH₃)—, —T—Ar¹ or —T—Ar¹—Q—, where Ar¹ represents optionally substituted arylene, heteroarylene, cycloalkylene or heterocycloalkylene, n represents the numbers 0, 1 or 2, Q represents oxygen or sulphur, R³ represents hydrogen, cyano or respectively optionally substituted alkyl, alkoxy, alkylthio, alkylamino, dialkylamino or cycloalkyl, and R⁴ represents hydrogen, hydroxyl, cyano or respectively optionally substituted alkyl, alkoxy or cycloalkyl, and R⁵ represents hydrogen or alkyl, and T represents a single bond, represents oxygen, sulphur, —CH₂—O—, —CH₂—S— or represents optionally substituted alkanediyl, R¹ represents alkoxy, R² represents cyano, thiocyanato, alkylcarbonyl, alkoxycarbonyl, aminocarbonyl, aminothiocarbonyl, alkylaminocarbonyl or dialkylaminocarbonyl, and Z represents respectively optionally substituted alkyl, alkenyl, alkynyl, cycloalkyl, aryl or heterocyclyl or a grouping

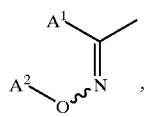

in which

A¹ represents alkyl having 1 to 4 carbon atoms or cycloalkyl having 1 to 6 carbon atoms, and A² represents optionally cyano-, alkoxy-, alkylthio-, alkylamino-, dialkylamino- or phenyl-substituted alkyl having 1 to 4 carbon atoms, alkenyl or alkynyl having in each case 2 to 4 carbon atoms.

2. Compounds of the formula (I) according to claim 1 in which

Ar represents optionally substituted phenylene or naphthylene, the substituents being selected from the list below:

halogen, cyano, nitro, amino, hydroxyl, formyl, carboxy, carbamoyl, thiocarbamoyl, straight-chain or branched alkyl, alkoxy, alkylthio, alkylsulphinyl or alkylsulphonyl having in each case 1 to 6 carbon atoms, straight-chain or branched alkenyl, alkenyloxy or alkinyloxy having in each case 2 to 6 carbon atoms, straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, straight-chain or branched halogenoalkenyl or halogenoalkenyloxy having in each case 2 to 6 carbon atoms and 1 to 11 identical or different halogen atoms, straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, alkylene or dioxyalkylene, each of which has 1 to 6 carbon atoms, is doubly attached and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms, E represents =CH— or nitrogen, G represents a single bond, represents oxygen, sulphur or represents respectively optionally halogen-, hydroxyl-, $C_1$–$C_4$-alkyl-, $C_1$–$C_4$-halogenoalkyl- or $C_3$–$C_6$-cycloalkyl-substituted alkanediyl, alkenediyl, alkinediyl having in each case up to 4 carbon atoms or one of the groupings below, —Q—CQ—, —CQ—Q—, —CH₂—Q—; —Q—CH₂—, —CQ—Q—CH₂—, —CH₂—Q—CQ—, —Q—CQ—CH₂—, —Q—CQ—Q—CH₂—, —N=N—, —S(O)ₙ—, —CH₂—S(O)ₙ—, —CQ—, —(O)ₙ—CH₂—, —C(R³)=N—O—, —C(R³)=N—O—CH₂—, —N(R⁴), —CQ—N(R⁴)—, —N(R⁴)—CQ—, —Q—CQ—N(R⁴)—, —N=C(R³)—Q—CH₂—, —CH₂—O—N=C(R³)—, —C(CH₃)—O—N=C(R³)—, —N(R⁴)—CQ—Q—, —CQ—N(R⁴)—CQ—Q—, —N(R⁴)—CQ—Q—CH₂—, —Q—C(R³)=N—O—CH₂—, —N(R⁴)—C(R³)=N—O—CH₂—, —O—CH₂—C(R³)=N—O—CH₂—, —N=N—C(R³)=N—O—CH₂—, —C(=N—R⁵)—C(R³)=N—OCH₂—, —C(=N—O—R⁵)—C(R³)—O—N=CH—, —C(=N—O—R⁵)—C(R³)—O—N=C(CH₃)—, —T—Ar¹ or —T—Ar¹—Q—, where n represents the numbers 0, 1 or 2, Q represents oxygen or sulphur, R³ represents hydrogen, cyano, represents respectively optionally halogen-, cyano- or $C_1$–$C_1$-alkoxy-substituted alkyl, alkoxy, alkylthio, alkylamino or dialkylamino having in each case 1 to 6 carbon atoms in the alkyl groups or represents respectively optionally halogen-, cyano-, carboxy-, $C_1$–$C_1$-alkyl- or $C_1$–$C_1$-alkoxy-carbonyl-substituted cycloalkyl having 3 to 6 carbon atoms, and R⁴ represents hydrogen, hydroxyl, cyano or represents optionally halogen-, cyano- or $C_1$–$C_1$-alkoxy-substituted alkyl having 1 to 6 carbon atoms or represents optionally halogen-, cyano-, carboxy-, $C_1$–$C_4$-alkyl- or $C_1$–$C_4$-alkoxy-carbonyl-substituted cycloalkyl having 3 to 6 carbon atoms, and R⁵ represents hydrogen or alkyl having 1 to 4 carbon atoms, Ar¹ represents phenylene, naphthylene, cycloalkylene, each of which is optionally mono- or polysubstituted by identical or different substituents, or represents heteroarylene or heterocycloalkylene having 3 to 7 ring members, at least one of which represents oxygen, sulphur or nitrogen and one or two more optionally represent nitrogen, the possible substituents being selected from the list below:

halogen, cyano, nitro, amino, hydroxyl, formyl, carboxy, carbamoyl, thiocarbamoyl;

respectively straight-chain or branched alkyl, alkoxy, alkylthio, alkylsulphinyl or alkylsulphonyl having in each case 1 to 6 carbon atoms;

respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 11 identical or different halogen atoms;

respectively straight-chain or branched alkylamino, dialkylamino, alkylcarbonyl, alkylcarbonyloxy, alkoxycarbonyl, alkylsulphonyloxy, hydroximinoalkyl or alkoximinoalkyl having in each case 1 to 6 carbon atoms in the individual alkyl moieties, and; cycloalkyl having 3 to 6 carbon atoms and T represents a single bond, represents oxygen, sulphur, —CH$_2$—O—, —CH$_2$—S— or represents alkanediyl having 1 to 3 carbon atoms, R$^1$ represents alkoxy, R$^2$ represents cyano, thiocyanato, aminocarbonyl, aminothiocarbonyl, or represents alkylcarbonyl, alkoxycarbonyl, alkylaminocarbonyl or dialkylaminocarbonyl having 1 to 4 carbon atoms in the respective alkyl chains, Z represents alkyl having 1 to 8 carbon atoms which is optionally mono- or polysubstituted by identical or different substituents selected from the group consisting of halogen, cyano, hydroxyl, amino, C$_1$–C$_4$-alkoxy, C$_1$–C$_4$-alkylthio, C$_1$–C$_4$-alkylsulphinyl and C$_1$–C$_4$-alkylsulphonyl (each of which is optionally substituted by halogen);

represents respectively optionally halogen-substituted alkenyl or alkynyl having in each case up to 8 carbon atoms;

represents cycloalkyl having 3 to 6 carbon atoms each of which is optionally mono- or polysubstituted by identical or different substituents selected from the group consisting of halogen, cyano, carboxy, phenyl (which is optionally substituted by halogen, cyano, C$_1$–C$_4$-alkyl, C$_1$–C$_4$-halogenoalkyl, C$_1$–C$_4$-alkoxy or C$_1$–C$_4$-halogenoalkoxy), C$_1$–C$_4$-alkyl and C$_1$–C$_4$-alkoxy-carbonyl;

represents phenyl, naphthyl, each of which is optionally mono- or polysubstituted by identical or different substituents, or represents heterocyclyl having 3 to 7 ring members, at least one of which represents oxygen, sulphur or nitrogen and one or two more optionally represent nitrogen, the substituents being selected from the list below: halogen, cyano, nitro, amino, hydroxyl, formyl, carboxy, carbamoyl, thiocarbamoyl;

respectively straight-chain or branched alkyl, alkoxy, alkylthio, alkylsulphinyl or alkylsulphonyl having in each case 1 to 6 carbon atoms; respectively straight-chain or branched alkenyl or alkenyloxy having in each case 2 to 6 carbon atoms;

respectively straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms;

respectively straight-chain or branched halogenoalkenyl or halogenoalkenyloxy having in each case 2 to 6 carbon atoms and 1 to 11 identical or different halogen atoms;

respectively straight-chain or branched alkylamino, dialkylamino, alkylcarbonyl, alkylcarbonyloxy, alkoxycarbonyl or alkylsulphonyloxy, having in each case 1 to 6 carbon atoms in the individual alkyl moieties;

alkylene or dioxyalkylene, each of which has 1 to 6 carbon atoms, is doubly attached and is optionally mono- or polysubstituted by identical or different halogens and/or straight-chain or branched alkyl having 1 to 4 carbon atoms and/or straight-chain or branched halogenoalkyl having 1 to 4 carbon atoms and 1 to 9 identical or different halogen atoms;

cycloalkyl having 3 to 6 carbon atoms;

cyclyl or heterocyclyl-methyl having in each case 3 to 7 ring members, 1 to 3 of which are in each case identical or different hetero nitrogen, oxygen and/or sulphur atoms, or a grouping

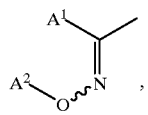

in which

A$^1$ represents alkyl having 1 to 4 carbon atoms or cycloalkyl having 1 to 6 carbon atoms, and A$^2$ represents optionally cyano-, alkoxy-, alkylthio-, alkylamino-, dialkylamino- or phenyl-substituted alkyl having 1 to 4 carbon atoms, alkenyl or alkynyl having in each case 2 to 4 carbon atoms.

3. Compounds of the formula (I) according to claim 1 in which

Ar represents ortho-, meta- or para-phenylene, each of which is optionally mono- or disubstituted by fluorine, chlorine, cyano, methyl, ethyl, cyclopropyl, trifluoromethyl, methoxy, ethoxy, methylthio, methylsulphinyl or methylsulphonyl, E represents =CH— or nitrogen, G represents oxygen or represents respectively optionally fluorine-, chlorine- or bromine-substituted dimethylene (ethane-1,2-diyl), ethene-1,2-diyl or one of the groupings below —Q—CQ—, —CQ—Q—, —CH$_2$—Q—; —Q—CH$_2$—, —CQ—Q—CH$_2$—, —CH$_2$—Q—CQ—, —Q—CQ—CH$_2$—, —Q—CQ—Q—CH$_2$—, —N=N—, —S(O)$_n$—, —CH$_2$—S(O)$_n$—, —CQ—, —S(O)$_n$,—CH$_2$—, —C(R$^3$)=N—O—, —C(R$^3$)=N—O—CH$_2$—, —N(R$^4$)—, —CQ—N(R$^4$)—, —N(R$^4$)—CQ—, —Q—CQ—N(R$^4$)—, —N=C(R$^3$)—Q—CH$_2$—, —CH$_2$—O—N=C(R$^3$)—, —C(CH$_3$)—O—N=C(R$^3$)—, —N(R$^4$)—CQ—Q—, —CQ—N(R$^4$)—CQ—Q—, —N(R$^4$)—CQ—Q—CH$_2$—, —Q—C(R$^3$)=N—O—CH$_2$—, —N(R$^4$)—C(R$^3$)=N—O—CH$_2$—, —O—CH$_2$—C(R$^3$)=N—O—CH$_2$—, —N=N—C(R$^3$)=N—O—CH$_2$—, —C(=N—O—R$^5$)—C(R$^3$)=N—OCH$_2$—, —C(=N—O—R$^5$)—C(R$^3$)—O—N=CH—, —C(=N—O—R$^5$)—C(R$^3$)—O—N=C(CH$_3$)—, —T—Ar$^1$ or —T—Ar$^1$—Q—, where n represents the numbers 0, 1 or 2, Q represents oxygen or sulphur, R$^3$ represents hydrogen, cyano, methyl, ethyl or cyclopropyl, and R$^4$ represents hydrogen, methyl, ethyl or cyclopropyl, R$^5$ represents hydrogen or alkyl having 1 to 4 carbon atoms, Ar$^1$ represents phenylene or pyridinediyl, each of which is optionally mono- to trisubstituted by identical or different substituents, represents respectively optionally monosubstituted pyrimidinediyl, pyridazinediyl, pyrazinediyl, 1,2,3-triazinediyl, 1,2,4-triazinediyl or 1,3,5-triazinediyl or represents 1,2,4-thiadiazolediyl, 1,3,4-thiadiazolediyl, 1,2,4-oxadiazolediyl, 1,3,4-oxadiazolediyl, the substituents being selected from the list below:

fluorine, chlorine, bromine, cyano, methyl, ethyl, n- or i-propyl, cyclopropyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethyl-sulphonyl, and T represents a single bond, represents oxygen, sulphur, —CH$_2$—O—, CH$_2$—S—, methylene, ethylene or propylene, R$^1$ represents methoxy, ethoxy, n- or i-propoxy-, R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, Z represents phenyl, 1,2,4-thiadiazolyl, 1,3,4-thiadiazolyl, 1,2,4oxadiazolyl, 1,3,4-oxadiazolyl, pyridinyl, pyrimidyl, pyridazinyl, pyrazinyl, 1,2,3-triazinyl, 1,2,4-triazinyl or 1,3,5-triazinyl, each of which is optionally mono- to trisubstituted by identical or different substituents, the possible substituents being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methylenedioxy, ethylenedioxy, each of which is doubly attached and each of which is optionally mono- to tetrasubstituted by identical or different substituents selected from the group consisting of fluorine, chlorine, methyl, trifluoromethyl and, or a grouping

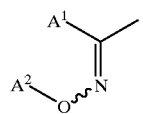

in which

A$^1$ represents methyl, ethyl, n- or i-propyl, n-, i-, s- or t-butyl, cyclopropyl or cyclobutyl, A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

4. Compounds of the formula (I) according to claim 1 in which

Ar represents ortho-phenylene,

E represents =CH— or nitrogen,

G represents —O—CH$_2$—,

R$^1$ represents methoxy,

R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, and Z represents phenyl which is in each case optionally mono- to trisubstituted by identical or different substituents, the substituents being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methylenedioxy or ethylenedioxy, each of which is doubly attached and each of which is optionally mono- to tetrasubstituted by identical or different substituents selected from the group consisting of fluorine, chlorine, methyl, trifluoromethyl or ethyl, or a grouping

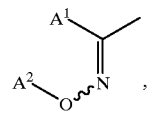

in which

A$^1$ represents methyl, ethyl, n- or i-propyl, n-, i-, s- or t-butyl, cyclopropyl or cyclobutyl, and A$^2$ represents methyl, ethyl, n- or i-propyl, n-, i-, s- or t-butyl, allyl, propargyl, but-2-en-1-yl, 2-methyl-prop-1-en-3-yl, cyanomethyl, methoxymethyl, ethoxymethyl, methoxyethyl, ethoxyethyl, methylthiomethyl, ethylthiomethyl, methylthioethyl, ethylthioethyl, dimethylaminomethyl, dimethylaminoethyl, methylaminomethyl, methylaminoethyl or benzyl.

5. Compounds of the formula (I) according to claim 1 in which

Ar represents ortho-phenylene,

E represents =CH— or nitrogen,

G represents —C(R$^3$)=N—O—CH$_2$—,

R$^3$ represents methyl,

R$^1$ represents methoxy or methylamino,

R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, and Z represents phenyl, pyridyl or pyrimidyl, each of which is optionally mono- to trisubstituted by identical or different substituents, the substituents being selected from the list below:

fluorine, chlorine, bromine, cyano, methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl or ethylsulphonyl, trifluoromethyl, trifluoroethyl, difluoromethoxy, trifluoromethoxy, difluorochloromethoxy, trifluoroethoxy, difluoromethylthio, trifluoromethylthio, difluorochloromethylthio, trifluoromethylsulphinyl or trifluoromethylsulphonyl, methoxycarbonyl, ethoxycarbonyl, methoximinomethyl, ethoximinomethyl, methoximinoethyl, ethoximinoethyl, methylenedioxy or ethylenedioxy, each of which is doubly attached and each of which is optionally mono- to tetrasubstituted by identical or different substituents selected from the group consisting of fluorine, chlorine, methyl, trifluoromethyl and ethyl.

6. Compounds of the formula (I) according to claim 1 in which

Ar represents ortho-phenylene,

E represents =CH— or nitrogen,

G represents oxygen or —T—Ar$^1$—O—,

Ar$^1$ represents 1,2,4-thiadiazolediyl, 1,3,4-thiadiazolediyl, 1,2,4-oxadiazolediyl, 1,3,4-oxadiazolediyl or represents pyridinediyl, pyrimidinediyl or 1,3,5-triazinediyl, each of which is optionally mono- or disubstituted by identical or different substituents selected from the group consisting of fluorine, chlorine, cyano, methyl, cyclopropyl, methoxy, methylthio, trifluoromethyl, difluoromethoxy, and difluorochloromethoxy, R$^1$ represents methoxy, R$^2$ represents cyano, thiocyanato, aminocarbonyl, aminothiocarbonyl, acetyl, propionyl, pivaloyl, methoxycarbonyl, ethoxycarbonyl, methylaminocarbonyl, ethylaminocarbonyl or dimethylaminocarbonyl, T represents a single bond, represents oxygen, sulphur, —CH$_2$—O—, CH$_2$—S—, methylene, ethylene or propylene, and Z represents phenyl, pyridyl, pyrimidyl or thienyl, each of which is optionally mono- to trisubstituted by identical or different substituents selected from the group consisting of fluorine, chlorine, bromine, cyano, methyl, ethyl, n- or i-propyl, n-, i-, s- or t-butyl, trifluoromethyl, methoxy, ethoxy, n- or i-propoxy, difluoromethoxy, difluorochloromethoxy, trifluoroethoxy, trifluoromethoxy and methylenedioxy or ethylenedioxy, each of which is doubly attached and each of which is optionally mono- to tetrasubstituted by identical or different substituents selected from the group consisting of fluorine, chlorine, methyl, trifluoromethyl and ethyl.

7. Process for preparing pesticides, characterized in that compounds of the formula (I) according to claim 1 are mixed with extenders and/or surfactants.

8. A pesticidal composition comprising a pesticidally effective amount of at least one compound of the formula (I) according to claim 1 and a diluent.

9. A pesticidal composition comprising a pesticidally effective amount of at least one compound of the formula (I) according to claim 1 and an extender and/or surfactant.

10. A method of combating pests comprising applying a pesticidally effective amount of a compound of the formula (I) according to claim 1 to the pests or their habitat.

* * * * *